United States Patent
Zhou et al.

(10) Patent No.: US 11,786,525 B1
(45) Date of Patent: Oct. 17, 2023

(54) HIGH-EFFICIENCY ANTI-TUMOR NANO-DRUG DELIVERY SYSTEM CONTAINING HYDRALAZINE AND PREPARATION METHOD THEREOF

(71) Applicant: SHANGHAI INSTITUTE FOR ADVANCED STUDY ZHE JIANG UNIVERSITY, Shanghai (CN)

(72) Inventors: Ruhong Zhou, Stormville, NY (US); Lianxue Zhang, Hangzhou (CN)

(73) Assignee: SHANGHAI INSTITUTE FOR ADVANCED STUDY ZHE JIANG UNIVERSITY, Shanghai (CN)

( * ) Notice: Subject to any disclaimer, the term of this patent is extended or adjusted under 35 U.S.C. 154(b) by 0 days.

(21) Appl. No.: 18/116,817

(22) Filed: Mar. 2, 2023

(30) Foreign Application Priority Data

Aug. 31, 2022 (CN) .......................... 2022110513925

(51) Int. Cl.
| | |
|---|---|
| *A61K 31/502* | (2006.01) |
| *A61K 31/704* | (2006.01) |
| *A61K 9/51* | (2006.01) |
| *A61P 35/00* | (2006.01) |
| *B82Y 5/00* | (2011.01) |
| *B82Y 40/00* | (2011.01) |

(52) U.S. Cl.
CPC .......... *A61K 31/502* (2013.01); *A61K 9/5161* (2013.01); *A61K 9/5192* (2013.01); *A61K 31/704* (2013.01); *A61P 35/00* (2018.01); *B82Y 5/00* (2013.01); *B82Y 40/00* (2013.01)

(58) Field of Classification Search
CPC ....... A61K 31/50; A61K 9/5161; A61P 35/00; B82Y 5/00; B82Y 40/00
See application file for complete search history.

(56) References Cited

FOREIGN PATENT DOCUMENTS

| CN | 103301472 A | 9/2013 |
|---|---|---|
| CN | 104523598 A | 4/2015 |

OTHER PUBLICATIONS

Liu et al., cRGD-modified benzimidazole-base pH-responsive for enhanced tumor targeted doxorubicin delivery, ACS Paragon Plus Environment, p. 1-27 (Year: 2016).*
Cao Dongling, et al., "Stimulus-responsive camptothecin/ doxorubicin prodrug based on dextran for combined treatment of cancer", China Excellent Master's Thesis Full-text Database Engineering Science and Technology Series 1, 2017, pp. 1-9.
(Continued)

*Primary Examiner* — Carlos A Azpuru
(74) *Attorney, Agent, or Firm* — Zhigang Ma (57) ABSTRACT

A high-efficiency anti-tumor nano-drug delivery system containing hydralazine (hydralazine-nanoparticles abbreviated as H-NPs) is provided. The drug delivery system takes hydralazine and doxorubicin combined by a π-π bond as a hydrophobic core and takes dextran as a hydrophilic shell. The high-effective anti-tumor nano-drug delivery system containing hydralazine can increase the vascular permeability and blood perfusion of the tumor site, improve the enrichment and penetration of nanoparticles in the tumor, reduce tumor hypoxia, increase the sensitivity of the tumor to a chemotherapy drug doxorubicin, and significantly improve its anti-tumor effect by expanding the tumor blood vessels and regulating tumor microenvironment (TME).

5 Claims, 7 Drawing Sheets

(56) References Cited

OTHER PUBLICATIONS

Jinjian Liu et al., "cRGD modified benzimidazole-based pH-responsive nanoparticles for enhanced tumor targeted doxorubicin delivery", ACS Paragon Plus Environment, 2016, pp. 1-27.
CNIPA, Notification of a First Office Action for CN202211051392.5, dated Oct. 17, 2022.
Shanghai Institute for Advanced Study of Zhe Jiang University (Applicant), Reply to Notification of a First Office Action for CN202211051392.5, dated Oct. 25, 2022, w/ (allowed) replacement claims, Oct. 28, 2022.
CNIPA, Notification to grant patent right for invention in CN202211051392.5, dated Nov. 4, 2022.

\* cited by examiner

HIGH-EFFICIENCY ANTI-TUMOR NANO-DRUG DELIVERY SYSTEM CONTAINING HYDRALAZINE AND PREPARATION METHOD THEREOF

TECHNICAL FIELD

The disclosure relates to the technical field of biomedical materials, and more particularly to a high-efficiency anti-tumor nano-drug delivery system containing hydralazine with potential of hydrogen (pH) responsiveness and tumor targeting.

BACKGROUND

According to the China Cancer Registry Annual Report in 2017, cancer has become the leading cause of death for Chinese residents. At present, although a variety of new tumor treatment methods have been emerging for many years, chemotherapy based on small molecule drugs (doxorubicin, camptothecin, etc.) is still the main method for clinical treatment of tumors. These small molecule drugs have problems such as poor water solubility or structural stability, unsatisfactory pharmacokinetics and biological distribution, resulting in low enrichment concentration of effective drugs in tumor tissue, while most of the drugs are distributed in healthy tissues and organs of patients and cause serious toxic side effects, which reduces the quality of life and immunity of patients, thus limiting the clinical use dosage of drugs and the continuity of treatment, and finally leading to the current situation that chemotherapy had too much toxic and side effects on patients to achieve the expected treatment effects.

Nanoparticle drug delivery systems hold great promise for cancer treatment. Due to the enhanced permeability and retention (EPR) effect of tumor sites, chemotherapy based on nanoparticle-delivered drugs can greatly prolong the blood circulation time of drug molecules in the human body, thereby enhancing the retention and enrichment of nanoparticles in the tumor sites. In addition, it is difficult for the nanoparticles to seep from the dense normal capillaries, which reduces the distribution of drugs in normal tissues and greatly reduces the systemic toxicity caused by missed targets of chemotherapy drugs. Compared with traditional small molecule chemotherapy drugs, the above advantages of the nanoparticles can reduce the side effects of drugs on patients and improve the drug tolerance dose of cancer patients. For example, doxorubicin HCl liposome injection (DOXIL) reduces the enrichment of doxorubicin in the heart of patients, thereby avoiding the fatal toxicity of doxorubicin to the heart. In recent years, nano preparations such as DOXIL and nanoparticle albumin-bound paclitaxel (ABRAXANE) have been used in clinical applications, and many other macromolecular nano-drugs are at various stages of clinical trials. However, compared with the free original drugs, the clinical research results show that most of the nano-drugs currently used in the clinic can only reduce the toxic and side effects of drugs to patients, and only a few nanoparticle drug delivery systems show good therapeutic effects on tumors, which also led to the ultimate failure of many nano-drugs in clinical trials. Therefore, further design and preparation of nano-drugs to improve the therapeutic effects on tumors is an urgent problem to be solved in the field of drug delivery.

Through further clinical research, the in vivo delivery process of tumor-targeted nano-drugs is a five-step "CAPIR cascade" process from circulation in the blood circulation system (circulation), accumulation into tumor tissues (accumulation), penetration into the tumor tissue (penetration), cellular internalization via endocytosis or fusion (internalization), and release of intracellular drugs (release), high efficiency in every step is the key to obtain the high efficacy of nano-drugs in the tumor treatment. Scholars at home and abroad have done a lot of work in long circulation C, improving cellular internalization I and intracellular release R, but the accumulation A of nano-drugs in tumor sites and the penetration P in the tumor tissues are still bottlenecks. This is because: 1) the tortuous vascular system which is characteristic of the tumor microenvironment (TME), is a major obstacle to the delivery of nanoparticles. The tortuous vascular system at the tumor site causes the blood vessels at the tumor site to become narrow, reduces the blood flow, and reduces the enrichment of nanoparticles at the tumor site. 2) In addition, the increased interstitial fluid pressure (IFP) and abnormal extracellular matrix (ECM) form the second physical barrier. Because the size of nano-drugs ranges from a few nanometers to more than 100 nanometers, and the diffusion rate is inversely proportional to the size, the diffusion ability of such large-size nano-drugs is far less than that of small molecule drugs, which further weakens the penetration of nanoparticles in the tumor site, resulting in the accumulation of nanoparticles only in the surrounding area the tumor vascular system. Therefore, the nanoparticles usually cannot reach deep tumor cells far from the vascular system. 3) Tumor interstitial cells, intercellular matrix, and tumor-associated fibroblasts (TAFs) form the third physical barrier. In most tumors, the barrier of intercellular matrix limits the diffusion of macromolecular drugs and nanoparticles in tumors. Tumors with interstitial proliferation usually have the characteristics of containing a large number of interstitial cells, which secrete fibronectin and collagen, resulting in high osmotic pressure. In this situation, the interstitial cells are also obstacles to the interstitial penetration of nanoparticles. TAFs, as a major component of stromal cells, are the most abundant cells in tumors, especially in pancreatic cancer and breast cancer. TAFs promote tumor growth, invasion, and metastasis by remodeling ECM, secreting growth factors and cytokines, and inhibiting immune response.

Therefore, improving the massive enrichment of nano-drugs at tumor sites and their permeability in tumor tissues to well complete the five-step delivery process of CAPIR is the key to improving the anti-tumor efficacy of nano-drugs. In response to these problems, scientists have carried out a lot of exploration work. For example, losartan, an angiotensin inhibitor, has been reported to reduce interstitial collagen, thereby improving the oxygen permeability inside the tumor and increasing the delivery of nanoparticles. Abnormal TME can help cancer cells escape from the immune system and increase their invasion and metastasis potential, while a vascular remodeling strategy can inhibit the extravasation of blood components to reduce the interstitial fluid pressure of tumor tissues, promoting the delivery of nanoparticles in the tumor sites. It is proposed that the use of angiogenesis inhibitors can normalize the tumor vascular system, improve blood perfusion, reduce tumor hypoxia, and increase the enrichment of drugs in the tumor sites. The anti-angiogenesis strategy reconstructs the structural integrity and function of the tumor pressure gradient by restoring the tumor blood vessels, thus effectively promoting the delivery of nanoparticles at the tumor sites. Vasodilator agents can also increase blood perfusion, vascular density, leakage, and expansion, thus improving the efficacy of chemotherapy. In addition, therapeutic strategies for ECM or vascular remodeling can also promote the extravasation and permeation of drugs and nanoparticles. For example, the reduction of the interstitial components of tumor by collagenase (EMC-regulatory enzyme), lysine oxidase inhibitory antibody, hyaluronidase, or transforming growth factor-beta (TGF-β) inhibitors, the permeability of macromolecules in tumor can be increased and the penetration of nanoparticles can be enhanced, thus enhancing the efficacy of chemotherapy.

SUMMARY

In view of the defects in the above background, the disclosure expands tumor blood vessels and regulates tumor microenvironment (TME) through hydralazine-nanoparticles (H-NPs), thus increasing the vascular permeability and blood perfusion of tumor sites, improving the enrichment and penetration of nanoparticles in tumor, reducing tumor hypoxia, increasing the sensitivity of tumor to chemotherapy drug doxorubicin, and significantly improving its anti-tumor effect.

The disclosure adopts the following technical solutions.

Specifically, a highly-efficiency anti-tumor nano-drug delivery system containing hydralazine (HDZ) is provided. The drug delivery system takes the HDZ and doxorubicin (DOX) combined by a π-π bond as a hydrophobic core and takes dextran (Dex) as a hydrophilic shell.

The disclosure also discloses a preparation method of the highly-efficiency anti-tumor nano-drug delivery system containing hydralazine, including the following steps:

step (1), preparing Dex-hyd-DOX/cRGD, including:
preparing doxorubicin with an azide end-group, and then performing a clicking chemical method to make the doxorubicin with the azide end-group and cRGD be reacted with an alkynyl-modified dextran to form the Dex-hyd-DOX/cRGD; wherein the cRGD is a cyclic octapeptide containing an RGD sequence. The RGD sequence is composed of arginine (abbreviated as R), glycine (abbreviated G) and aspartic acid (abbreviated as D); and step (2), preparing the drug carrier system, including:
adding Dex-hyd-DOX/cRGD and the HDZ into ultra-pure water, stirring for dissolution at 600 revolutions per minute (r/min) to obtain a mixed solution, and then performing ultrasonic treatment; stirring while performing the ultrasonic treatment by using an intermittent ultrasonic method until the mixed solution turns reddish brown, and stopping the ultrasonic treatment; continuing to stir until a red solution is obtained, and then dialyzing the red solution by using a dialysis bag (molecular weight cut off abbreviated as MWCO: 3500 Dalton abbreviated as Da) to dialysis for about one day (24-30 h) to obtain the high-effective anti-tumor nano-drug carrier system containing hydralazine.

In an embodiment, in the step (1), a molar ratio of the doxorubicin with the azide end-group:the cRGD:the alkynyl-modified dextran is 2.51:1:4.58. A mass ratio of Dex-hyd-DOX/cRGD to HDZ is 10-13.3:1. In this situation, the average number of the DOX combined on each Dex chain is 1.1, and the average number of the cRGD is 0.6. This cannot only ensure a suitable nano-drug delivery system can be prepared, but also ensure that the HDZ is loaded as much as possible. Because if there is too much doxorubicin and the hydrophobic core formed by the combination of doxorubicin and HDZ is too large, the particle size of nanoparticles will become larger, and the hydrophobicity of nanoparticles is too strong, which is easy to form aggregation.

In an embodiment, in the intermittent ultrasonic method, ultrasonic parameters include: 120 voltages (V) of ultrasonic voltage, 20 kilohertz (kHz) of ultrasonic frequency, and 20 seconds of the ultrasonic treatment at 5 second intervals.

The beneficial effects of the disclosure are as follows.

According to the disclosure, the cRGD polypeptide dextran-doxorubicin prodrug (i.e., Dex-hyd-DOX/cRGD) with potential of hydrogen (pH) responsiveness and tumor targeting is first prepared, and then the nanoparticles (H-NPs) are formed through taking the HDZ and the doxorubicin the hydrophobic core combined through the π-π bond and taking the dextran as the hydrophilic shell. H-NPs can not only increase the enrichment of nanoparticles in tumor sites by dilating blood vessels, but also regulate tumor microenvironment and enhance the effect of chemotherapy on tumor. H-NPs can prolong the blood circulation time of HDZ in vivo, enhance the enrichment of HDZ in the tumor site through the EPR effect, and actively target and enrich H-NPs to the tumor site through the cRGD polypeptide on the surface of H-NPs, thereby reducing the toxic and side effects of HDZ off-target on the human body. In addition, H-NPs release encapsulated HDZ in the acidic microenvironment of the tumor to expand tumor blood vessels and regulate TME, which can further enhance the enrichment and penetration of drugs in the tumor site. In this disclosure, HDZ and DOX have stronger binding force through π-π binding, which effectively overcomes the defect that the encapsulated hydralazine is easy to leak in the blood (with reference to the following literature for details: Jinjian Liu et al., "cRGD modified benzimidazole-based pH-responsive nanoparticles for enhanced tumor targeted doxorubicin delivery", ACS Paragon Plus Environment, 2016, pp 1-27.), so that it can be released at the tumor site and the tumor microenvironment can be effectively improved.

DETAILED DESCRIPTION OF EMBODIMENTS

The disclosure is further described below in combination with the attached drawings and specific embodiments.

Embodiment 1

Specifically, a high-effective anti-tumor nano-drug delivery system containing hydralazine is provided, and the specific preparation process is as follows.

Synthesis of Dextran Propargyl Carbonate (Dex-C≡C)

Before the experiment, the glassware required for the reaction is put into the oven for drying in advance. 14.34 grains (g) (88.5 millimoles abbreviated as mmol) of N, N'-carbonyldiimidazole abbreviated as CDI are weighed and added into a round bottom flask, then 50 milliliters (mL) of dichloromethane are poured into the round bottom flask and fully stirred. Then, 3.61 g (51.6 mmol) of 3-Butyn-1-ol ($C_4H_6O$) is weighed and added to a constant pressure dropping funnel, and dissolved by adding 30 mL of dichloromethane into the constant pressure dropping funnel. The solution in the constant pressure dropping funnel is added dropwise to the round bottom flask and reacted at room temperature for 1 hour (h) to obtain a reaction solution. The reaction solution is extracted three times with saturated sodium chloride aqueous solution, the organic phase is collected, dried overnight with anhydrous sodium sulfate ($Na_2SO_4$), and filtered. Finally, dichloromethane solvent is removed by rotary evaporation to obtain a crude product of alkynyl butyl carbonyl imidazole.

2 g (0.05 mmol) of dextran is weighed and added into a side-neck flask and dissolved by adding 20 mL of dimethyl sulfoxide (DMSO) into the side-neck flask. 0.317 g (1.5 mmol) of alkynyl butyl carbonyl imidazole is weighed and dissolved with 8 mL of DMSO to obtain a mixed solution, the mixed solution is transferred to a constant pressure dropping funnel, then slowly dropped into the alkynyl butyl carbonyl imidazole solution, and reacted for 24 h at 70° C., thereby obtaining a product solution. The product solution is dialyzed with double-distilled water ($ddH_2O$) for 2 days to remove unreacted alkynyl butyl carbonyl imidazole and DMSO through a cellulose tubular membrane (molecular weight cut off abbreviated as MWCO 2000 Dalton abbreviated as Da). Finally, alkynyl-modified dextran (Dex-C≡C) is obtained by freeze-drying (1.464 g, yield: 63.2%).

Preparation of Hydrazone Bond Modified Doxorubicin Containing Nitrogen End-Group (DOX-Hyd-$N_3$)

Before the experiment, the glassware required for the reaction is put into an oven at 120° C. for drying in advance. 102.4 mg ($6.02 \times 10^{-1}$ mmol) of 6-azidohexyl hydrazide and 118.8 mg ($2.04 \times 10^{-1}$ mmol) of DOX·HCl are weighed and added into a round bottom flask, dissolved by measuring and adding 30 mL of anhydrous methanol, a drop of glacial acetic acid is dropped into the round bottom flask, then 113.8 mg of anhydrous sodium sulfate is weighed and added therein, and a serpentine condenser tube (water condensation) is connected to the mouth of the round bottom flask, and the reaction is carried out at 60° C. for 24 h in the dark. After the reaction, the reaction solution is concentrated to 6 mL by rotary evaporation, and then 30 mL of anhydrous ether is added and fully mixed. The dark red solid crude product is obtained by centrifugation, and finally the DOX-hyd-$N_3$ product is obtained by vacuum drying. Then the crude product is washed again with anhydrous ether until the unreacted 6-azidohexyl hydrazide is removed, and finally the final pure DOX-hyd-$N_3$ product (110.0 mg, yield: 73.3%) is obtained.

Dex-Hyd-DOX/cRGD Synthesis

Figure 7:
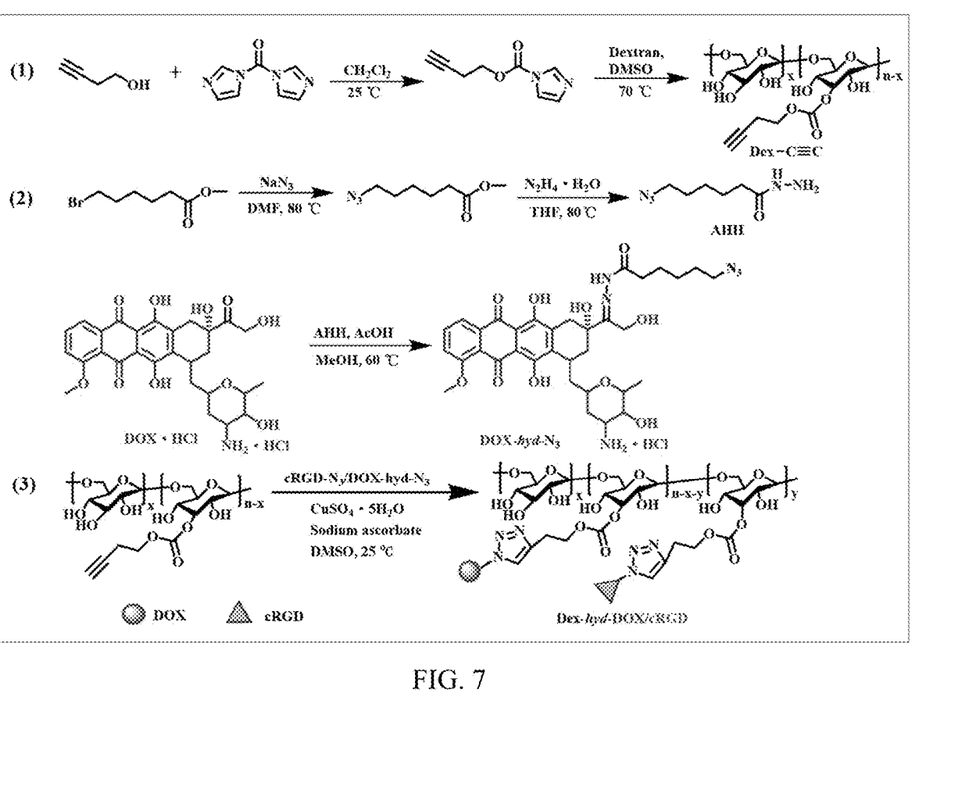
FIG. 7 illustrates a chemical flowchart of preparing Dex-hyd-DOX/cRGD.

The doxorubicin-dextran pre-drug (Dex-hyd-DOX/cRGD) is prepared by "click" chemical reaction through DOX-hyd-$N_3$, cRGD-PEG2000-$N_3$ and Dex-C≡C (as shown in FIG. 7).

Firstly, 9.79 mg (0.0682 mmol) of $CuBr_2$ and 23.66 mg (0.1365 mmol) of N, N, N', N'', N'''-pentamethyldiethylenetriamine (PMDETA) are weighed and dissolved in 6 mL of DMSO and reacted for 10 min under nitrogen atmosphere. 0.2 g (0.0374 mmol) of Dex-C≡C and 0.02 g (0.0149 mmol) of cRGD-PEG2000-$N_3$ are added respectively and stirred at room temperature for 8 h, and then 50 mg (0.0683 mmol) of DOX-hyd-$N_3$ is weighed and stirred for 8 h. After the reaction, the mixed solution is dialyzed with DMSO for 12 h to remove the unreacted DOX-hyd-$N_3$ and cRGD-PEG2000-$N_3$, and then dialyzed with ultrapure water for 48 h to remove DMSO. Finally, the red solid product Dex-hyd-DOX/cRGD (0.232 g, yield: 85.4%) is obtained by freeze-drying.

Construction of H-NPs Anti-Tumor Nano-Drug Delivery System 16 mg Dex-hyd-DOX/cRGD and 1.6 mg HDZ are dissolved in 2 mL of ultrapure water. After moderate stirring, ultrasonic treatment is carried out for 10 min. Intermittent ultrasonic method (model of ultrasonic cell crusher: KC-250W, ultrasonic voltage: 120 V, ultrasonic frequency: 20 KHz, interval of 5 seconds, ultrasonic 20 seconds) is used, ultrasonic treatment is performed while stirring until the solution becomes reddish brown, and then the ultrasonic treatment is stopped. Finally, the solution is stirred for another 4 h, the solution turns red, then the solution is dialyzed with a dialysis bag (MWCO: 3500 Da) for one day. The final red solution of H-NPs with a mass ratio of Dex-hyd-DOX/cRGD to HDZ of 10:1 is obtained.

Embodiment 2

The difference from the embodiment 1 is that the preparation of H-NPs anti-tumor nano-drug delivery system is as follows.

16 mg Dex-hyd-DOX/cRGD and 1.4 mg HDZ are dissolved in 2 mL of ultrapure water, mixed moderately, and then subjected to ultrasonic treatment for 10 min. The intermittent ultrasonic method is used (model of ultrasonic cell crusher: KC-250W, ultrasonic voltage: 120 V, ultrasonic frequency: 20 KHz, interval of 5 seconds, ultrasonic 20 seconds). The ultrasonic treatment is performed while stirring until the solution turns reddish brown, and the ultrasonic treatment is stopped. Finally, the solution is stirred for another 4 h, the solution turns red, and then dialyzed with a dialysis bag (MWCO: 3500 Da) for 28 h. The final red solution of H-NPs with a mass ratio of Dex-hyd-DOX/cRGD to HDZ of 11.4:1 is obtained.

Embodiment 3

The difference from the embodiment 1 is that the preparation of H-NPs anti-tumor nano-drug delivery system is as follows.

16 mg Dex-hyd-DOX/cRGD and 1.2 mg HDZ are dissolved in 2 mL of ultrapure water, mixed moderately, and then subjected to ultrasonic treatment for 10 mi. The intermittent ultrasonic method is used (model of the ultrasonic cell crusher: KC-250W, ultrasonic voltage: 120 V, ultrasonic frequency: 20 KHz, interval of 5 seconds, ultrasonic 20 seconds). The ultrasonic treatment is performed while stirring until the solution turns reddish brown, and the ultrasonic treatment is stopped. Finally, the solution is stirred for another 4 h, and then dialyzed with a dialysis bag (MWCO: 3500 Da) for 30 h. The final red solution of H-NPs with a mass ratio of Dex-hyd-DOX/cRGD to HDZ of 13.3:1 is obtained.

The Dex-hyd-DOX/cRGD and H-NPs synthesized in the embodiment 1 are characterized as follows.

1) Characterization of Dex-Hyd-DOX/cRGD

Figure 1:
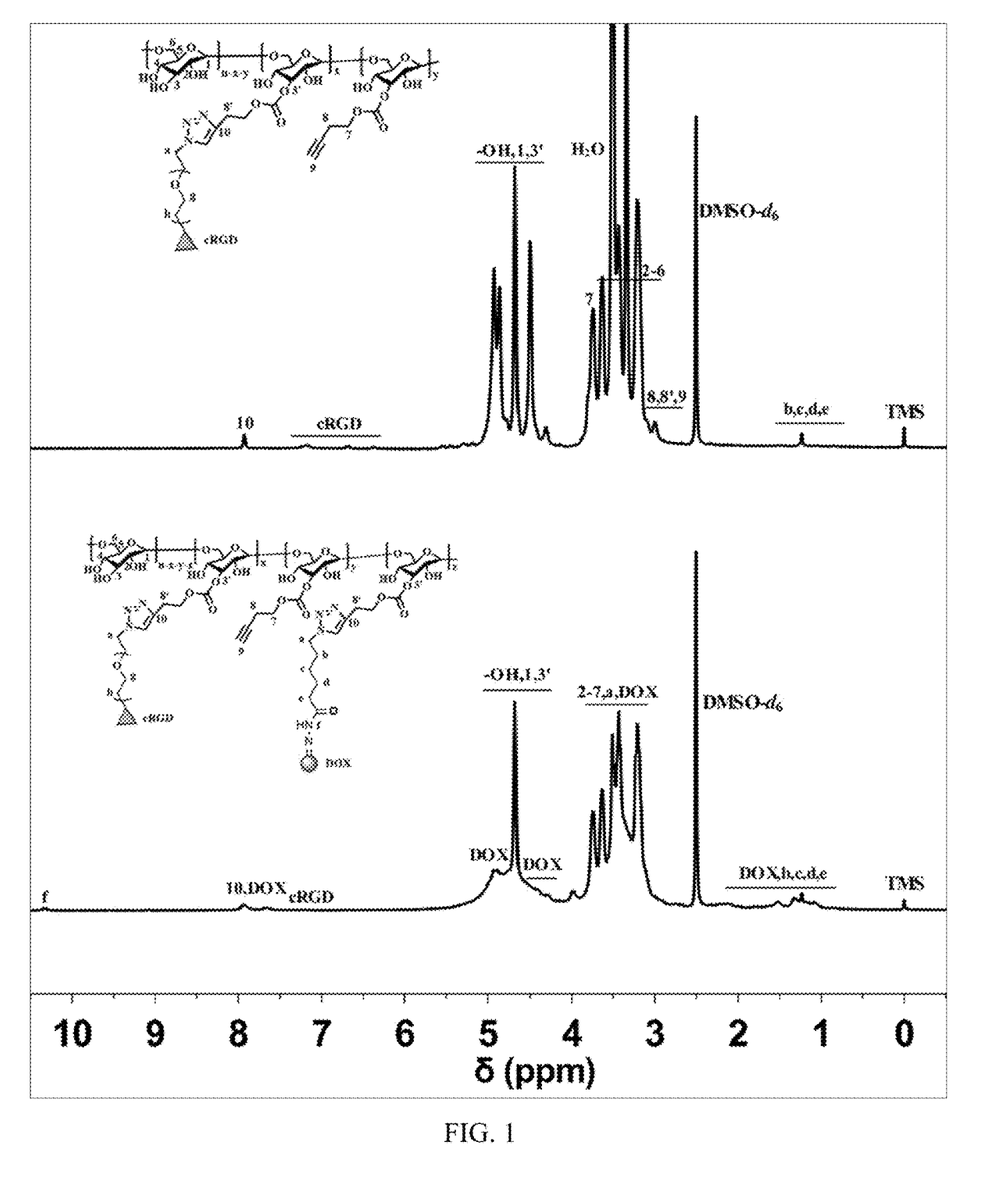
FIG. 1 illustrates a schematic diagram showing proton ($^1$H) nuclear magnetic resonance (NMR) of Dex-hyd-cRGD and Dex-hyd-DOX/cRGD.

Chemical structures of Dex-hyd-cRGD and Dex-hyd-DOX/cRGD are analyzed using $^1$H NMR. As shown in FIG. 1, it can be seen that the protons on the structures of the Dex-hyd-cRGD and Dex-hyd-DOX/cRGD can find corresponding chemical shifts, which proves the successful synthesis of Dex-hyd-DOX/cRGD. The mass percentage of cRGD in polymer Dex-hyd-cRGD is determined to be 9.5% by a bicinchoninic acid (BCA) method. The content of DOX in polymer Dex-hyd-DOX/cRGD is determined to be 11.2% by ultraviolet spectrometry. Dex (i.e., dextran, with an average molecular weight of 5000). In Dex-hyd-DOX/cRGD: when Dex is a chain, the average number of DOX is 1.1, and the average number of cRGD is 0.6. This ratio can not only ensure a suitable nano-drug delivery system can be prepared, but also ensure that HDZ is loaded as much as possible. Because if there is too much doxorubicin, the hydrophobic core formed by the combination of doxorubicin and HDZ is too large, the particle size of nanoparticles will be larger, and the hydrophobicity of nanoparticles is too strong, which is easy to form aggregation.

2) Characterization of H-NPs

Dex-hyd-DOX/cRGD and HDZ are assembled into H-NPs with DOX and HDZ as hydrophobic cores.

As amphiphilic copolymers, Dex-hyd-DOX and Dex-hyd-DOX/cRGD copolymers self-assemble into D-NPs and C-NPs in an aqueous solution.

Figure 2A:
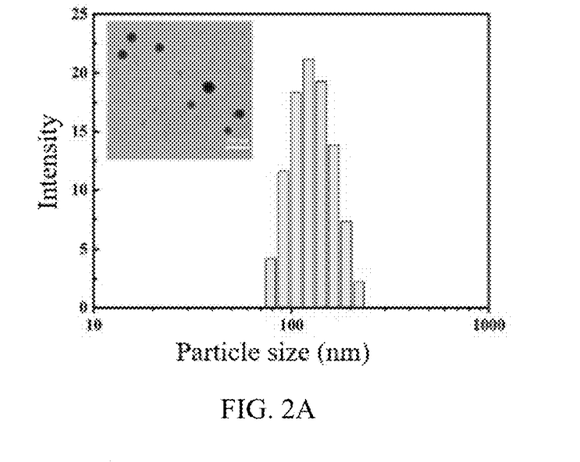
FIG. 2A illustrates a schematic diagram showing hydralazine-nanoparticles (H-NPs) by transmission electron microscope (TEM) and dynamic light scattering (DLS).
Figure 2B:
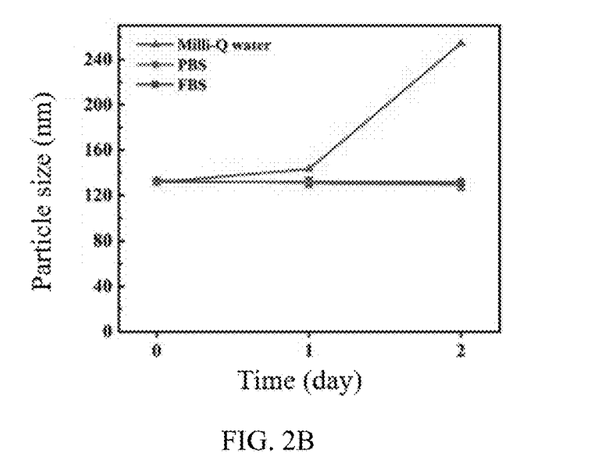
FIG. 2B illustrates a schematic diagram showing results of stability test of the H-NPs.

The particle size, particle size distribution, and potential of nanoparticles are determined by dynamic light scatter. The results are shown in Table 1. There is no significant difference in the particle size of the three nanoparticles. However, their charge varies greatly. D-NPs have a strong negative charge, while C-NPs and H-NPs have a weak positive charge. The morphology of H-NPs is observed by transmission electron microscopy (TEM). As shown in FIG. 2A, H-NPs are spherical in shape. The H-NPs are further studied under three conditions (Milli-Q water, phase-buffered saline abbreviated as PBS, and fetal bovine serum abbreviated as FBS). As shown in FIG. 2B, the average diameter of H-NPs in PBS and FBS remains basically unchanged during the 2-day monitoring period, while the volume of H-NPs in the aqueous solution becomes larger. It indicates that the prepared H-NPs have good stability during the delivery of biological blood to the target tissue.

TABLE 1

Characterization of Dex-C≡C and three kinds of nanoparticles

| Group | Size(nm) | PDI | Zeta(mV) |
| --- | --- | --- | --- |
| Dex-C≡C | — | — | −11.9 |
| D-NPs | 111 | 0.187 | −8.64 |
| C-NPs | 117 | 0.231 | 0.81 |
| H-NPs | 130 | 0.223 | 1.64 |

In Vitro Drug Release of H-NPs

Figure 2C:
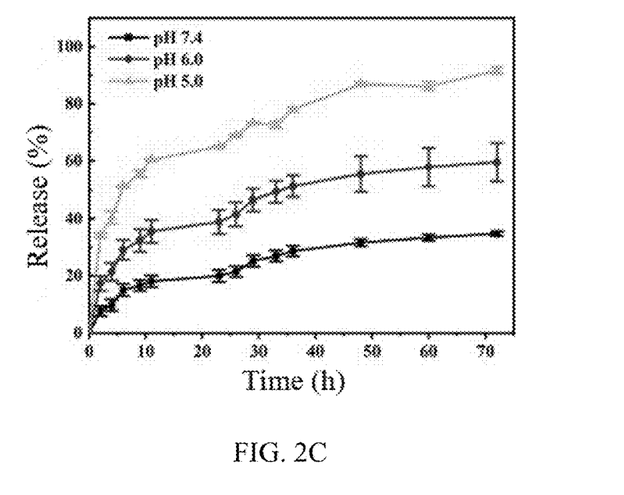
FIG. 2C illustrates a schematic diagram showing H-NPs release curve in vitro.

H-NPs solution is placed in three different buffer solutions (pH 7.4, pH 6.0, and pH 5.0), and the release behavior of DOX is studied under constant temperature oscillation at 37° C. Due to the weak acid environment in tumor cells, the hydrazone bond is easy to break. Therefore, DOX in Dex-hyd-DOX molecules can be released under acidic conditions. The cumulative release results are shown in FIG. 2C. With the decrease in pH value, the release rate of DOX increases, indicating that H-NPs have a good pH response. Therefore, H-NPs can achieve the effect of intelligent controlled release in the weak acidic environment of tumor cells. Because hydralazine and doxorubicin form a hydrophobic core by π-π bond, hydralazine will also be released together when doxorubicin is released.

Cytotoxicity

Figure 3A:
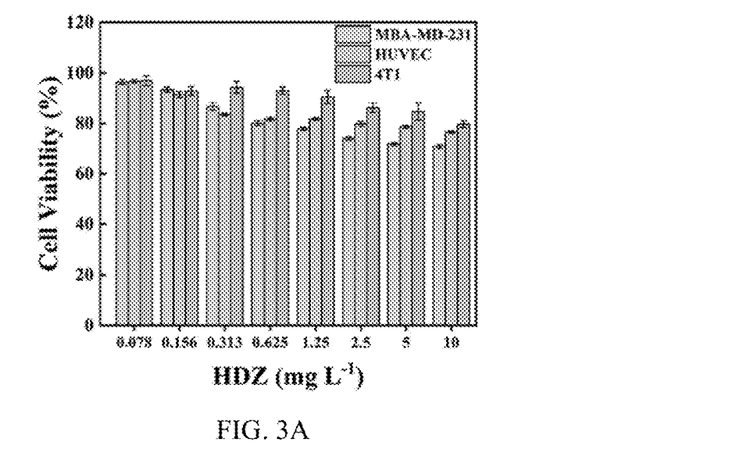
FIG. 3A illustrates a schematic diagram showing toxicity of HDZ to MBA-MD-231, HUVEC and 4T1 cells.
Figure 3B:
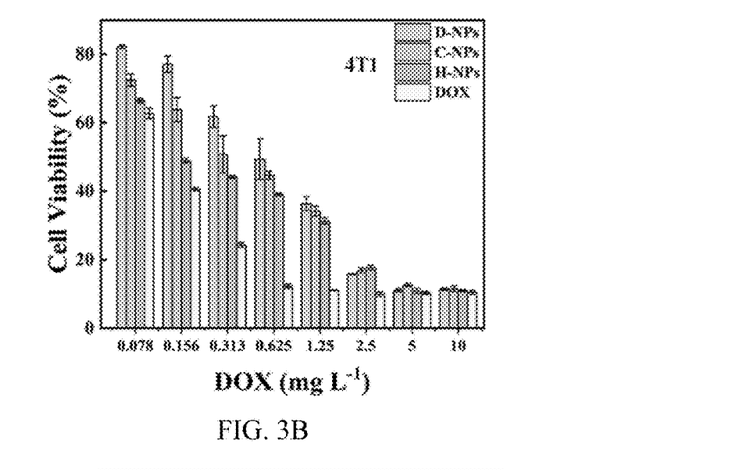
FIG. 3B illustrates a schematic diagram showing toxicity of D-NPs, C-NPs, the H-NPs and DOX to the 4T1 cells.
Figure 3C:
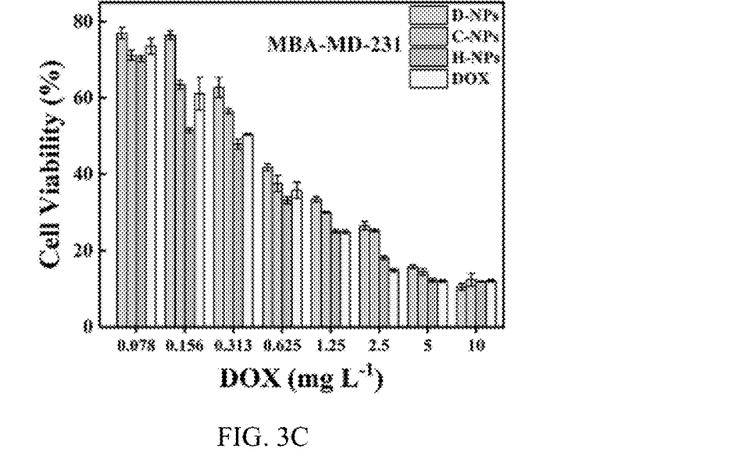
FIG. 3C illustrates a schematic diagram showing toxicity of the D-NPs, the C-NPs, the H-NPs and the DOX to the MBA-MD-231 cells.
Figure 3D:
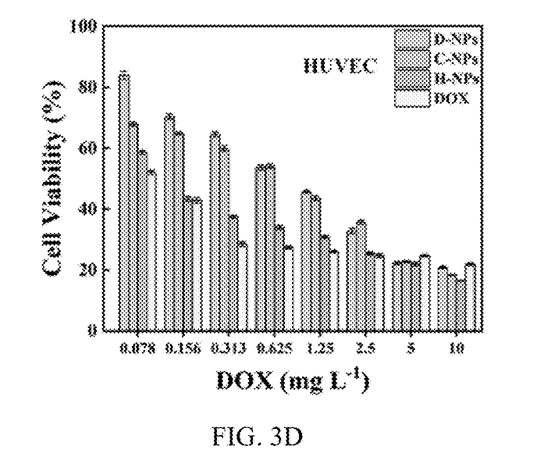
FIG. 3D illustrates a schematic diagram showing toxicity of the D-NPs, the C-NPs, the H-NPs and the DOX to the HUVEC cells.

At the cellular level, the cytotoxicity of HDZ to cells is first tested. HDZ at different concentrations is incubated with mouse breast cancer cells (4T1), human breast cancer cells (MBA-MD-231), and vascular epithelial cells (HU-VEC) for 48 h. The experimental results are shown in FIG. 3A, it can be seen that HDZ is not very toxic to the three kinds of cells. Then, the cytotoxicity of D-NPs, C-NPs, H-NPs, and DOX with 4T1, MBA-MD-231, and HUVEC cells is subsequently tested. The experimental results are shown in FIG. 3B, FIG. 3C and FIG. 3D. It can be seen that compared with D-NPs, C-NPs have stronger cytotoxicity to 4T1 cells and MBA-MD-231 cells, and there is little difference in the cytotoxicity on HUVEC. This is because there is a polypeptide cRGD on the surface of C-NPs targeting the integrin αvβ3 overexpressed on the surface of 4T1 and MBA-MD-231 tumor cells, which can make more C-NPs enter the tumor cells and improve their cytotoxicity. However, HUVEC cells have little difference in cytotoxicity between D-NPs and C-NPs because there is no overexpressed integrin αvβ3 on their surface. The toxicity of targeted H-NPs is stronger than that of D-NPs and C-NPs, indicating that the combination of HDZ and doxorubicin has a better effect on killing tumor cells.

Blood Circulation and Biodistribution

Figure 4A:
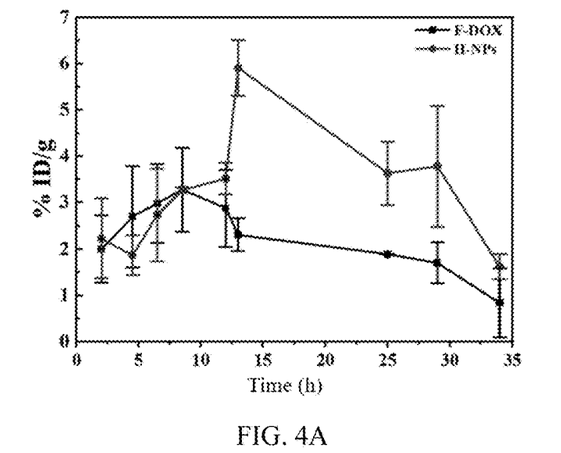
FIG. 4A illustrates a schematic diagram showing blood circulation time of free doxorubicin (F-DOX) and the H-NPs.

Generally, nanoparticles with a particle size less than 200 nm have a longer blood circulation time in the blood of organisms. In order to verify whether H-NPs have longer blood circulation time in the blood, H-NPs and free doxorubicin solution are injected into BALB/c mice via tail vein (high dose 7.5 mg/kg). The % ID/g values of H-NPs and free doxorubicin in the blood of mice at different times are shown in FIG. 4A. It can be found that compared with free drugs, H-NPs have longer blood circulation time and increase the accumulation of drugs in tumor sites.

Figure 4B:
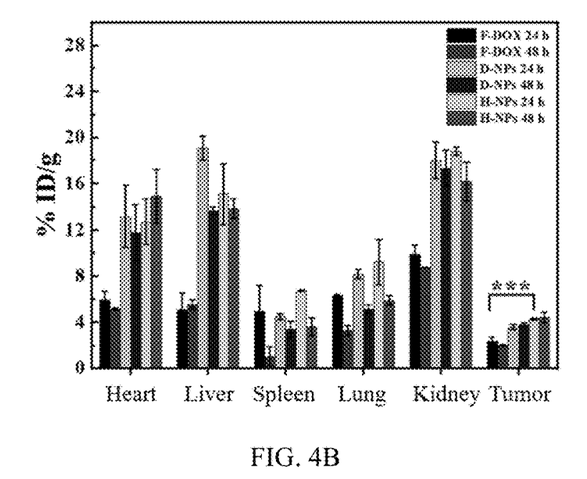
FIG. 4B illustrates a schematic diagram showing biodistribution of the free doxorubicin, the D-NPs and the H-NPs in mice at 24 h and 48 h.

In addition, in order to detect the difference in the distribution of free doxorubicin, D-NPs and H-NPs in tumors and other organs, 4T1 tumor-bearing mice are sacrificed at different time intervals after intravenous injection of different drugs, the organs of the mice are taken out for tissue grinding and extraction, and finally fluorescence analysis is performed. The experimental results are shown in FIG. 4B. It can be seen that compared with free doxorubicin, D-NPs and H-NPs have higher enrichment rates in various organs and tumors of mice, which are about 1.52 and about 1.81 times (24 h) higher than free doxorubicin, respectively. With the extension of time, the enrichment of D-NPs and H-NPs in the tumor site increases to some extent at 48 h, while the free doxorubicin decreases (about 1.92 and about 2.21 times of free doxorubicin). From the above cytotoxicity and blood circulation experiments, it can be inferred that this is because compared with free doxorubicin, D-NPs and H-NPs have longer blood circulation capacity in the blood and are not easy to be cleared by cells. Moreover, compared with D-NPs without targeting peptides, H-NPs targeting peptides have a better tumor enrichment effect at tumor sites.

Enhance the Accumulation of Nanoparticles in Tumors

Figure 5A:
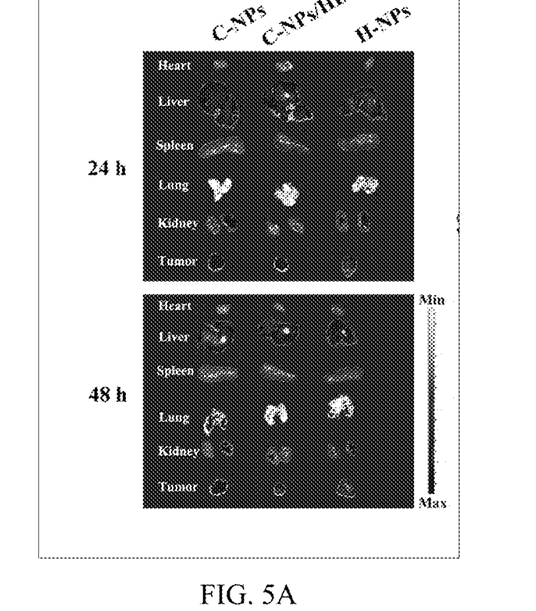
FIGS. 5A-5B illustrate biodistribution of the C-NPs, C-NPs/HDZ and the H-NPs in vivo.
Figure 5B:
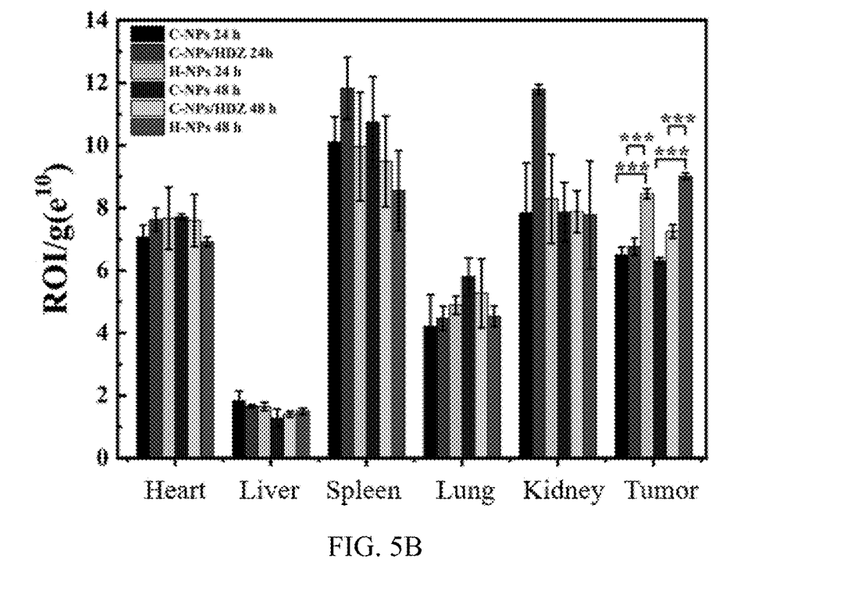

Tumor vasodilation and the reduction of TAFs caused by HDZ can create favorable conditions for the enrichment of nanoparticles in the tumor site and the penetration of drugs in tumor sites. In actual clinical practice, most cancers are not detected until the late stage of cancer, so that tumor-bearing mice with a tumor volume of about 300 mm$^3$ are used to simulate the real situation of actual clinical cancer patients. Three groups of mice bearing a breast cancer tumor model (tumor volume is about 300 mm$^3$) are given three different treatment schemes for two consecutive days: H-NPs, C-NPs/HDZ, C-NPs (HDZ: 7.5 mg/kg, DOX: 7.5 mg/kg). Then, various tissues of mice are taken out at different set time points for analysis to explore the accumulation, penetration, and distribution of HDZ on nanoparticles in tumors under different conditions (FIG. 5A). The DOX signal is detected by the small animal in vivo imager, and the DOX enrichment of the H-NPs group at 24 h is calculated to be about 1.04 and about 1.30 times that of C-NPs/HDZ and C-NPs, respectively (FIG. 5 B). At 48 h, the enrichment of DOX in tumor sites in H-NPs and C-NPs/HDZ groups is increased compared with that in C-NPs group, and the enrichment of DOX in H-NPs group is about 1.10 and about 1.36 times higher than that in C-NPs/HDZ and C-NPs, respectively. It can also be seen that the C-NPs/HDZ group also has higher DOX enrichment than the C-NPs group. This indicates that free HDZ can also enhance the enrichment of C-NPs in tumor sites. The H-NPs containing HDZ can enrich HDZ in tumor sites, and HDZ can greatly enhance the enrichment effect of H-NPs in tumor sites, thus forming a complementary effect. Similar experimental results are obtained by grinding mouse organs and tissues at different time points, and then analyzing them by fluorescence analysis. It speculated by the inventor that the reason is that H-NPs release encapsulated HDZ under the acidic microenvironment of the tumor to enhance the vascular vasodilation and repair the vascular system at the tumor site, thus enhancing the enrichment of H-NPs at the tumor site.

Regulation of Tumor Microenvironment (TME)

Figure 6:
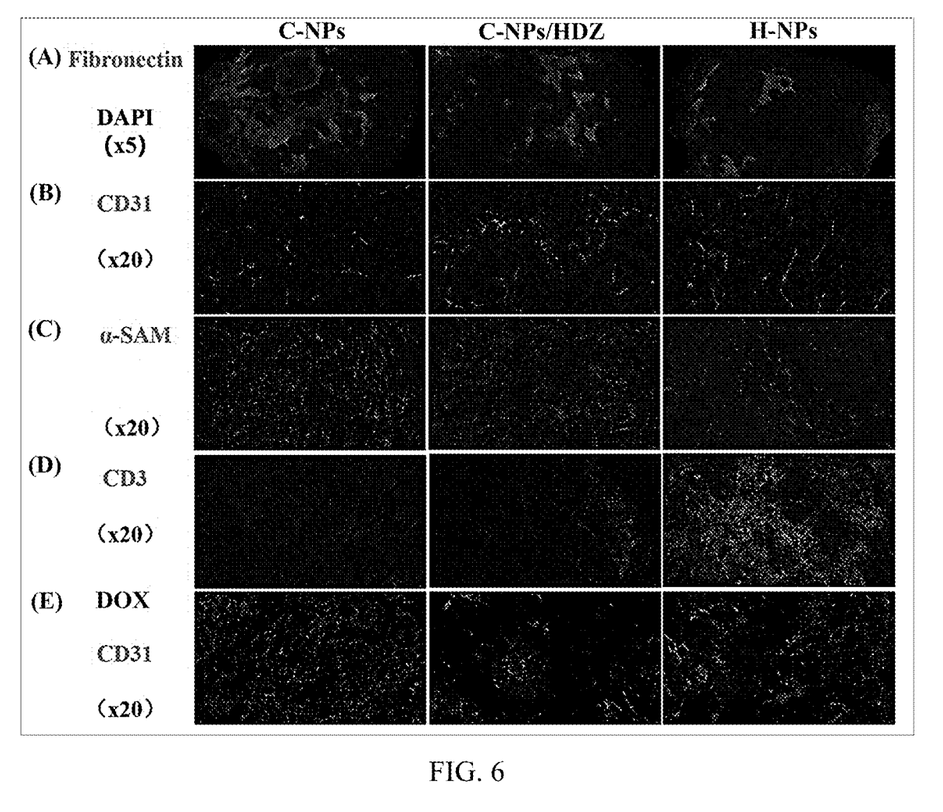
FIG. 6 illustrates a schematic diagram showing changes of tumor microenvironment (TME) in 4T1 tumor 48 hours after injection of drug in which a portion A shows the change of fibronectin, a portion B shows the change of tumor vessels, a portion C shows the change of smooth muscle α-actin, a portion D shows the change of immune T cells (CD3), a portion E shows the change of penetration of doxorubicin.

After the imaging experiment in mice, the tumor tissue sections and immunofluorescence staining are performed, and the number of fibronectin in the tumor microenvironment, tumor blood vessels, the number of smooth muscle α-actin (also referred to as α-SAM), the number of immune T cells (CD3) and the distribution of doxorubicin are detected to observe the effect of H-NPs on tumor microenvironment. The test results are shown in FIG. 6. The fibronectin is observed using ×5 magnification, which makes it is convenient to observe its distribution throughout tumor. Compared with the C-NPs group, the fibronectin of the C-NPs/HDZ group is reduced correspondingly, and the fibronectin of the H-NPs group almost completely disappears at the tumor site. The quantity of smooth muscle α-actin also changes similarly. It can be seen from the detection of tumor blood vessels that compared with the C-NPs group, the blood vessels of the C-NPs/HDZ group and the H-NPs group are dilated, and the dilating effect of the blood vessels of the H-NPs group is better than that of the C-NPs/HDZ group. Compared with the C-NPs group and the C-NPs/HDZ group, treatment with H-NPs results in a very significant increase in CD3+T cell infiltration in tumors. Finally, the penetration of DOX at the tumor site is detected. Compared with the C-NPs group, the DOX in the C-NPs/HDZ group has a certain penetration centered on the blood vessel, while the H-NPs group has a very obvious penetration of DOX, which could reach a far distance from the blood vessel. These experimental results show that H-NPs can well regulate the tumor microenvironment, promote the enrichment and penetration of nano-drugs in the tumor site, and also indicate that H-NPs has a good therapeutic effect on the tumor.

What is claimed is:

1. An anti-tumor nano-drug delivery system containing hydralazine (HDZ), wherein the anti-tumor nano-drug delivery system is hydralazine-nanoparticles (H-NPs) with a hydrophobic core of both doxorubicin and the hydralazine and is assembled by Dex-hyd-DOX/cRGD and the hydralazine together; and the Dex-hyd-DOX/cRGD is a cRGD polypeptide dextran-doxorubicin prodrug with pH responsiveness and tumor targeting.

2. A preparation method of the anti-tumor nano-drug delivery system containing hydralazine according to claim 1, comprising:
    step (1), preparing the Dex-hyd-DOX/cRGD, comprising:
        preparing doxorubicin with an azide end-group, and then performing a clicking chemical method to make the doxorubicin with the azide end-group and cRGD be reacted with an alkynyl-modified dextran to form the Dex-hyd-DOX/cRGD;
    step (2), dissolving the Dex-hyd-DOX/cRGD and the HDZ in ultrapure water to obtain a mixed solution, then stirring while performing ultrasonic treatment using an intermittent ultrasonic method until the mixed solution turns reddish brown, and stopping the ultrasonic treatment; continuing to stir until a red solution is obtained, and then dialyzing the red solution by using a dialysis bag with 3500 Dalton (Da) of molecular weight cut off (MWCO) for 24-30 hours to obtain the anti-tumor nano-drug delivery system containing hydralazine.

3. The preparation method according to claim 2, wherein in the step (1), a molar ratio of the doxorubicin with the azide end-group:the cRGD:the alkynyl-modified dextran is 2.51:1:4.58.

4. The preparation method according to claim 2, wherein in the step (2), a mass ratio of the Dex-hyd-DOX/cRGD to the HDZ is 10-13.3:1.

5. The preparation method according to claim 2, wherein in the step (2), ultrasonic parameters of the intermittent ultrasonic method comprise: 120 voltages (V) of ultrasonic voltage, 20 kilohertz (kHz) of ultrasonic frequency, and 20 seconds of the ultrasonic treatment at 5 second intervals.

* * * * *